(12) United States Patent
Lee et al.

(10) Patent No.: US 6,810,334 B2
(45) Date of Patent: Oct. 26, 2004

(54) METHOD FOR INSPECTING WAFER DEFECTS OF A SEMICONDUCTOR DEVICE

(75) Inventors: Hyun bae Lee, Seoul (KR); Jung Hwan Choi, Seoul (KR); Jeong Hun Kim, Eumsung-Kun (KR)

(73) Assignee: Dongbu Electronics Co., Ltd., Seoul (KR)

( * ) Notice: Subject to any disclaimer, the term of this patent is extended or adjusted under 35 U.S.C. 154(b) by 0 days.

(21) Appl. No.: 10/458,871

(22) Filed: Jun. 11, 2003

(65) Prior Publication Data

US 2003/0229457 A1 Dec. 11, 2003

(30) Foreign Application Priority Data

Jun. 11, 2002 (KR) .................................. 10-2002-0032613

(51) Int. Cl.$^7$ ............................................. G06F 19/00
(52) U.S. Cl. .............................. 702/35; 702/34; 702/81
(58) Field of Search ........................ 702/35, 40, 81.84, 702/117, 183, 188, 34; 700/103, 110; 382/141, 144, 149, 180; 356/237.2, 237.4

(56) References Cited

U.S. PATENT DOCUMENTS

| | | | | |
|---|---|---|---|---|
| 5,539,752 A | * | 7/1996 | Berezin et al. | 714/724 |
| 6,259,960 B1 | * | 7/2001 | Inokuchi | 700/110 |
| 6,334,097 B1 | * | 12/2001 | Yoshitake et al. | 702/185 |

* cited by examiner

*Primary Examiner*—Bryan Bui
(74) *Attorney, Agent, or Firm*—Grossman & Flight, LLC

(57) ABSTRACT

Disclosed is a method for inspecting defects of a wafer of a semiconductor device, wherein the wafer is set up with reference coordinates for a respective die so that inspection time is reduced and the defects are classified by the respective die. The method may be carried out by a defect analysis system comprising an inspection station for inspecting defects of the wafer and a review station for precisely re-inspecting defects. The method includes the steps of: providing the respective die with a serial number, the plural dies being formed on the wafer; and setting up coordinates for a plane of the respective die based on one edge of the die as reference point.

6 Claims, 4 Drawing Sheets

METHOD FOR INSPECTING WAFER DEFECTS OF A SEMICONDUCTOR DEVICE

TECHNICAL FIELD

The present disclosure relates to a method for inspecting wafer defects of a semiconductor device and, more particularly, to a method for inspecting wafer defects of a semiconductor device, wherein the wafers are set up with reference coordinates for respective die, and wherein defects are classified by respective die.

BACKGROUND

Recently, with development of semiconductor technology, a process control has been coming to the front, together with a technology for device design and unit process.

In order to increase a production yield of a semiconductor, it is helpful to minimize defects of the semiconductor by improving the process technology.

Accordingly, a series of processes for inspecting various defects generated and distributed on wafer during production process, for analyzing inspected defects, and for utilizing the analyzed information as material for process establishment of manufacturing equipment may be used together with the development of optimized process technology.

DETAILED DESCRIPTION OF EXAMPLE EMBODIMENTS

Generally, described herein is a method for inspecting defects on a wafer of a semiconductor device using a defect analysis system. The defect analysis system includes an inspection station for inspecting defects of the wafer and a review station for precisely re-inspecting defects. The method includes the steps of: providing a respective die with a serial number, the plural dies being formed on the wafer; and setting up coordinates for a plane of the respective die based on one edge of the die as reference point.

Preferably, the method also includes the step of classifying the dies depending on a size and a kind of defects after coordinates are set up for the plane of the respective die.

The disclosed method may be implemented through a setting-up of coordinates for a respective die thereby reducing inspection time, which makes it possible to inspect the entire area of a wafer.

Figure 1:
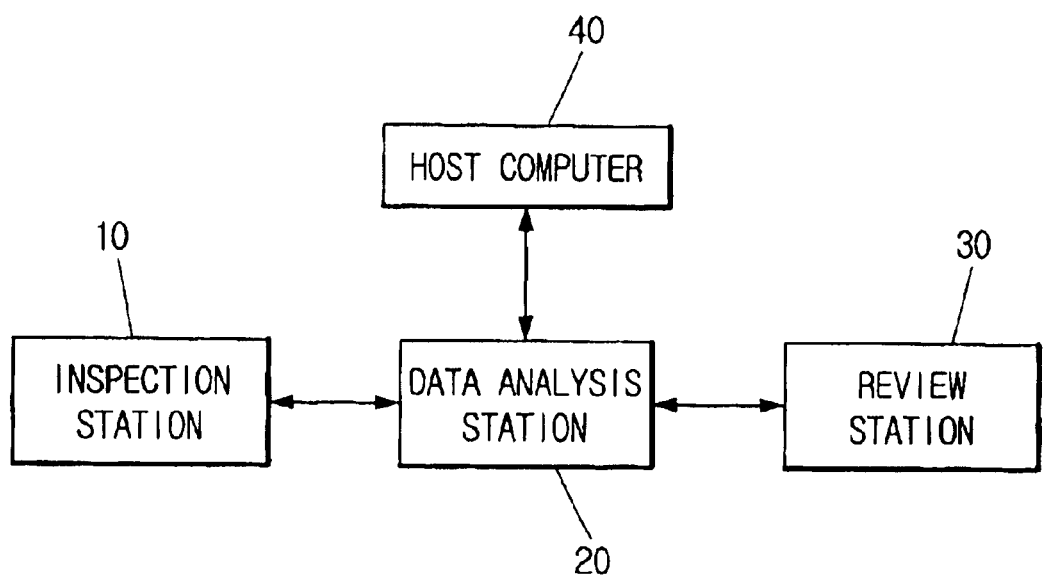
FIG. 1 is a block diagram of an example system for analyzing defects of wafer.

FIG. 1 is a block diagram illustrating a conventional system for analyzing defects of wafer. As shown in FIG. 1, the system comprises an inspection station 10, a data analysis station 20, a review station 30 and a host computer 40.

The inspection station 10 is a device for detecting a failure such as a defect generated on a wafer. The surface of the wafer is scanned to identify an identification cord of the wafer; to detect coordinates of a defective chip; and to determine the size of the defect.

The data analysis station 20 serves to calculate a defect density, a good chip rate, etc. from detection results of the inspection station 10.

The review station 30 serves to implement a more precise detection of defect, based on inspection data detected from the inspection station 10 if an operator determines a re-inspection is needed based on data from the inspection station 10. In addition, the review station 30 transmits the results of the re-inspection to the data analysis station 20.

The host computer 40 processes the result data of inspection of the defect. The result data is collected by the data analysis station 20, and serves to report the general analysis for control of an operation of respective manufacturing equipment introduced into the process lines.

The system for inspection of defects adapts an inspecting way that the inspection station 10 and the review station 30 set up coordinates of wafer for its entire area based on a specific die in the wafer so as to identify the position and size of the defects.

Figure 2:
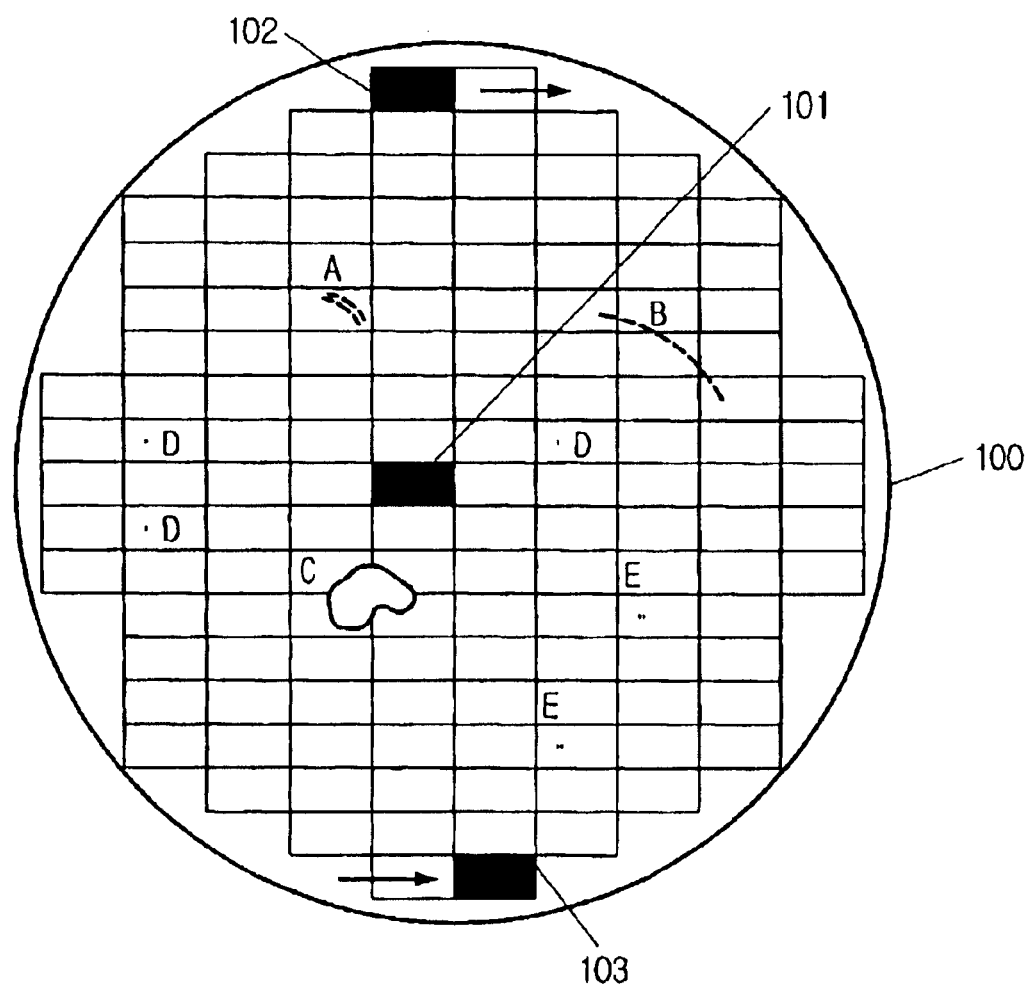
FIG. 2 is a schematic diagram of a wafer.

FIG. 2 is a schematic diagram of wafer illustrating a way for inspecting defects of wafer by an inspection station and a review station.

As shown in FIG. 2, there is a plurality of dies in the wafer 100. The inspection of a wafer is carried out from a start point, a first die 102 on upper side of the wafer to an end point, a last die 103 on lower side thereof. At this time, if a defect is detected during inspection, a specific die near a middle portion of the wafer is set as a reference die 101 so as to identify a position and a size of the defect. For example, the position of a defect is shown as follows, provided that a horizontal axis of the reference die 101 is X-axis and a vertical axis thereof is Y-axis.

TABLE 1

| Defects | X ($\mu$m) | Y ($\mu$m) |
|---|---|---|
| 1 | 10.879 | 198.456 |
| 2 | −17.333 | 178.333 |
| 3 | 17890.987 | 1999.899 |
| . | . | . |
| N | −180.000 | −200.6575 |

Meanwhile, various defects may be detected during inspection, which are described as follows. Group-type defect such as A of FIG. 2 is a plurality of defects generated during previous processes on a specific die. However, it causes problems in that the die having the defects A should be detected during inspection and it also requires repetitive inspections even after processing.

Liquid-type and scratch-type defects such as B and C are a plurality of defects generated along many dies, and they also require repetitive inspections. Defect D is a false defect, which should be detected during inspection. Defect D, however, may not be accurately detected during inspection. In the case of defect E, a cause and a kind of defect are not revealed so that it is processed as in the case of defect D and is possibly passed.

The reason why the problems during above-mentioned inspection are generated is that the entire wafer is inspected based on a specific reference die. Since the entire wafer is inspected with respect to a reference die, the inspect process is time-consuming.

Figure 3:
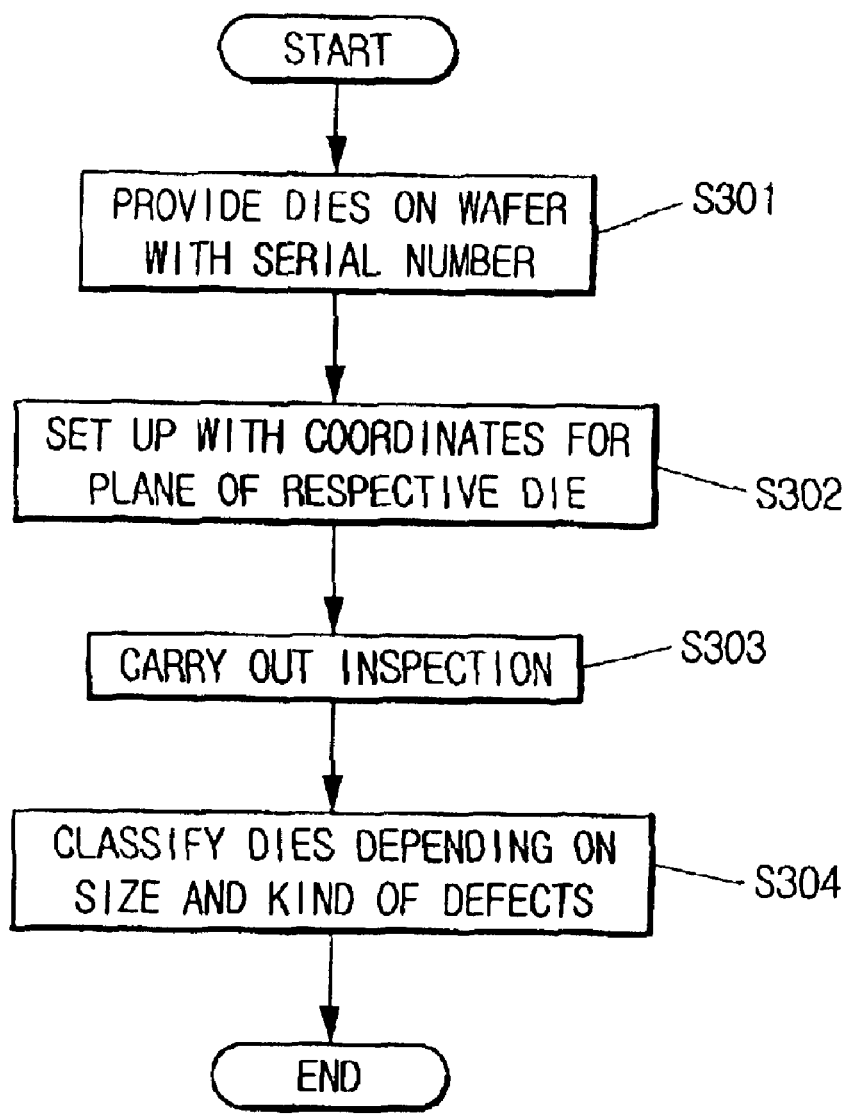
FIG. 3 is a flow chart illustrating an example wafer inspection method.
Figure 4:
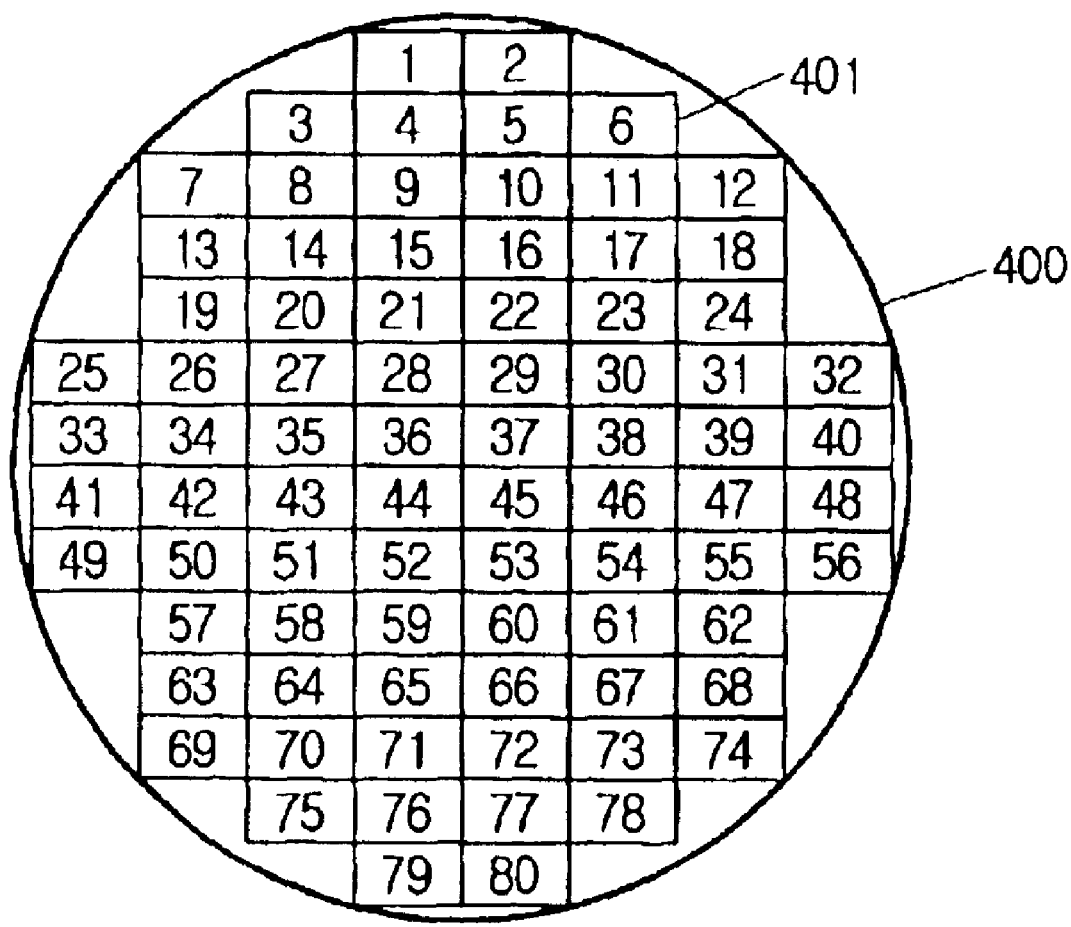
FIG. 4 is another schematic diagram of a wafer.

As shown in FIGS. 3 and 4, a wafer 400 includes a plurality of dies 401. Respective die 401 is provided a serial number (S301). Then, a plane of the respective die is set up with coordinates based on one edge of the die as a reference point (S302).

Defects of the wafer are inspected by the inspection method described herein (S303). An example result is as follows.

TABLE 2

| Die number | Position of defects | |
|---|---|---|
| | X ($\mu$m) | Y ($\mu$m) |
| 1 | 10 | 5 |
| 2 | 5 | 23 |
| 3 | 10 | 5 |
| . | . | . |
| . | . | . |
| . | . | . |
| N | 11 | 7 |

When the inspection method is carried out in a state where the respective die provided with a certain serial number is separately set up with coordinates, it may not require re-inspection for defective die that is detected on a previous process thereby to reducing the overall inspection time.

Also, in the conventional method, since the entire wafer is set up with coordinates based on a specific reference die, it causes a problem in that even though defects are inspected, it is difficult to identify exact positions of the defects. However, in the present system, the respective die is provided with a serial number, so that, when defects are generated, the die on which defects are generated is easily identified.

Meanwhile, the inspection method described herein is terminated when dies are classified by a size and a kind of defects according to inspection result (S304).

Since re-inspection for the defects detected on the previous process is not required, and it can inspect wafer for entire area, inspection time is reduced and yield rate is increased. Also, the dies are classified in accordance with a size and kind of the defects.

Although examples have been described for illustrative purposes, those skilled in the art will appreciate that various modifications, additions and substitutions are possible, without departing from the scope and spirit of the invention as disclosed in the accompanying claims.

What is claimed is:

1. A method for inspecting defects on a wafer of a semiconductor device using a defect analysis system comprising an inspection station for inspecting defects of the wafers, a review station for precisely re-inspecting defects, and a data analysis station for analyzing detection results, the method comprising:

providing each respective die on the wafer with a serial number, wherein a plurality of dies are formed on the wafer;

setting up coordinates for a plane of each respective die based on one edge of each respective die as reference point; and re-inspecting the defects at the review station, if precise re-inspection is required.

2. A method as defined in claim 1, further comprising classifying the die based on a size and a kind of defect associated with the die.

3. A method for determining the position of defects when inspecting defects on a wafer of a semiconductor device using a defect analysis system comprising an inspection station for inspecting defects of the wafer, and a review station for precisely re-inspecting defects, the method comprising:

providing each respective die on the wafer with a serial number, wherein a plurality of dies are formed on the wafer;

setting up coordinates for a plane of each respective die based on one edge of each respective die as reference point; and specifying the position of a defect detected by the defect analysis system with the serial number of the die on which the detected defect is located, and coordinate value of the defect on the respective coordinate set up for the plane of the respective die.

4. The method as defined in claim 3, further comprising classifying the die based on a size and a kind of defect associated with the die.

5. A method for inspecting defects on a wafer of a semiconductor device using a defect analysis system comprising an inspection station for inspecting defects of the wafer, a review station for precisely re-inspecting defects, and a data analysis station for analyzing detection results, the method comprising:

assigning a first die on the wafer a first serial number and a second die on the wafer a second serial number;

establishing a first coordinate for a plane of the first die based on one edge of the first die as first reference point;

setting up a second coordinate for a plane of the second die based on one edge of the second die as a second reference point; and inspecting the first die and the second die for defects.

6. A method as defined in claim 5, further comprising classifying the first die based on a size and a kind of defect associated with the first die.

* * * * *